(12) United States Patent
Chung et al.

(10) Patent No.: US 8,853,165 B2
(45) Date of Patent: Oct. 7, 2014

(54) PEPTIDE HAVING THE ABILITY TO REGENERATE BONE TISSUE AND FOR BINDING TO APATITE

(75) Inventors: Chong-Pyoung Chung, Seoul (KR); Yoon-Jeong Park, Seoul (KR); Sang Hoon Rhee, Seoul (KR); Jue-Yeon Lee, Gyeonggi-do (KR)

(73) Assignee: Nano Intelligent Biomedical Engineering Corporation Co., Ltd., Seoul (KR)

( * ) Notice: Subject to any disclaimer, the term of this patent is extended or adjusted under 35 U.S.C. 154(b) by 0 days.

(21) Appl. No.: 13/821,811

(22) PCT Filed: Mar. 9, 2011

(86) PCT No.: PCT/KR2011/001611
§ 371 (c)(1),
(2), (4) Date: Apr. 12, 2013

(87) PCT Pub. No.: WO2012/033268
PCT Pub. Date: Mar. 15, 2012

(65) Prior Publication Data
US 2013/0210736 A1 Aug. 15, 2013

(30) Foreign Application Priority Data
Sep. 10, 2010 (KR) .......... 10-2010-0088707

(51) Int. Cl.
| | |
|---|---|
| *A61P 19/08* | (2006.01) |
| *A61K 38/16* | (2006.01) |
| *A61K 38/10* | (2006.01) |
| *C07K 17/02* | (2006.01) |
| *C07K 17/14* | (2006.01) |
| *C07K 14/00* | (2006.01) |
| *C07K 7/08* | (2006.01) |
| *A61L 27/12* | (2006.01) |
| *A61L 27/22* | (2006.01) |
| *C07K 14/52* | (2006.01) |
| *A61L 27/54* | (2006.01) |

(52) U.S. Cl.
CPC ............. *C07K 14/52* (2013.01); *A61L 27/12* (2013.01); *A61L 2300/25* (2013.01); *A61L 27/22* (2013.01); *A61L 27/54* (2013.01)
USPC ....... 514/16.7; 514/21.3; 514/21.4; 514/21.5; 435/69.7; 530/324; 530/326; 530/327

(58) Field of Classification Search
CPC ....... A61L 27/12; A61L 27/54; A61L 27/227; C07K 14/51
See application file for complete search history.

(56) References Cited

U.S. PATENT DOCUMENTS

2004/0109937 A1* 6/2004 Jennissen et al. ............ 427/2.26

OTHER PUBLICATIONS

Brochmann, E., et al., "Bone morphogenetic protein-2 activity is regulated by secreted phosphoprotein-24 kd, an extracellular pseudoreceptor, the gene for which maps to a region of the human genome important for bone quality", "Metabolism Clinical and Experimental", May 2009, pp. 644-650, vol. 58.
He, X., et al., "Effect of Grafting RGD and BMP-2 Protein-Derived Properties to a Hydrogel Substrate on Osteogenic Differentiation of Marrow Stromal Cells", "Langmuir", Oct. 7, 2008, pp. 12508-12516, vol. 24.
Mitchell, E., et al., "Controlled spatial and conformational display of immobilised bone morphogenetic protein-2 and osteopontin signalling motifs regulates osteoblast adhesion and differentiation in vitro", "BMC Biology", May 10, 2010, pp. 1-12, vol. 8, No. 57.
Segvich, S., et al., "Identification of Peptides with Targeted Adhesion to Bone-Like Mineral via Phage Display and Computational Modeling", "Cells Tissues Organs", Aug. 14, 2008, pp. 245-251, vol. 189.

\* cited by examiner

*Primary Examiner* — Xiaozhen Xie
(74) *Attorney, Agent, or Firm* — Hultquist, PLLC; Steven J. Hultquist; Mary B. Grant

(57) ABSTRACT

The present invention relates to a peptide having bone tissue regeneration capacity and binding to a surface of apatite. More particularly, a peptide is provided having bone tissue regeneration capacity and specifically binding to a surface of apatite mineral, capable of being stably immobilized to the surface of apatite mineral to retain effective activity and exhibit bone regeneration effects for a long time, by linking an amino acid sequence having bone tissue regeneration capacity and an amino acid sequence having apatite-binding capacity to each other to thereby provide a peptide having both bone-forming effects and binding capacity to the surface of apatite mineral. A composition for bone tissue regeneration containing the peptide is further provided.

22 Claims, 3 Drawing Sheets

(a)

(b)

(c)

US 8,853,165 B2

PEPTIDE HAVING THE ABILITY TO REGENERATE BONE TISSUE AND FOR BINDING TO APATITE

CROSS-REFERENCE TO RELATED APPLICATIONS

This application is a U.S. national phase under the provisions of 35 U.S.C. §371 of International Patent Application No. PCT/KR11/001611 filed Mar. 9, 2011, which in turn claims priority of Korean Patent Application No. 10-2010-0088707 filed Sep. 10, 2010. The disclosures of such international patent application and Korean priority patent application are hereby incorporated herein by reference in their respective entireties, for all purposes.

BACKGROUND OF THE INVENTION

1. Field of the Invention

The present invention relates to a peptide having bone tissue regeneration capacity and specifically binding to a surface of apatite mineral, and more particularly, to a peptide having bone tissue regeneration capacity and specifically binding to a surface of apatite mineral, capable of being stably immobilized to the surface of apatite mineral to retain effective activity and exhibit bone regeneration effects for a long time, by linking an amino acid sequence having bone tissue regeneration capacity and an amino acid sequence having apatite-binding capacity to each other to thereby provide a peptide having both bone-forming effects and binding capacity to the surface of apatite mineral, and a composition for bone tissue regeneration, containing the peptide.

2. Background of the Related Art

Bones and teeth are called hard tissue in the body. Bones are composed of roughly 45% of bone inorganic materials, 35% of organic materials, and 20% of water. As for the tooth, enamel has about 97% inorganic material, dentin has 70% inorganic material, and cementum has 50% inorganic material. The inorganic material content is somewhat different depending on the animal species, body part, age, and the like.

Of the constituent materials, most of the organic materials are collagen, which is involved in generating bones and maintaining toughness and elasticity of the bones, and is present as a matrix that induces selective adhesion of bone cells to thereby orient bone inorganic particles. Apatite mineral is a main component of the bone in a natural state, that is, the bone inorganic materials of a vertebrate, and has been known as hydroxyapatite ($Ca_{10}(PO_4)_6(OH)_2$), hydroxylapatite, carbonated hydroxy apatite (CHAp, A-type: $Ca_{10}(PO_4)_6[(OH)_{2-2x}(CO_3)_x]$, B-type: $Ca_{10-x}[(PO_4)_{6-2x}(CO_3)_{2x}](OH)_2$). It has been known that a tiny amount of $Mg^{2+}$, $Na^+$, or $K^+$ is contained instead of $Ca^{2+}$, and a tiny amount of $Cl^-$ or $F^-$ is contained instead of $OH^-$. Therefore, studies that dental materials and bone graft materials for healing bone defects are made of apatite mineral or the surfaces thereof are coated with apatite mineral have been conducted.

The purpose of bone graft is to restore morphological and physiological functions of the bone to thereby maintain biomechanical roles. Hence, the apatite bone graft material used here needs to satisfy fundamental conditions, such as, being instantly used, having no immune responses, promoting fast bone generation and revascularization, maintaining bone support and continuity, and the like. However, apatite itself may serve as a mediator that has bone conductivity, but has no bone induction capacity for initial bon morphogenesis, which is needed to shorten the duration of treatment. In order to make up for this fault, studies that a biologically active substance having chemotactin, such as extracellular matrix protein, tissue growth factor, or bone morphogenetic protein, is used together with apatite were done, and products such as INFUSE (containing BMP-2), GEM21S (containing PDGF), and the like, were developed. However, these proteins are not stably immobilized on a surface of the apatite and released from the apatite, and then exposed to the systemic blood and thus be degraded, and therefore, activities of these proteins are difficult to maintain on the surface of the apatite for bone regeneration effect. Hence, a material which is stably immobilized on the surface of apatite to thereby retain effective activity is needed in order to increase the bone regeneration effect.

The present inventors made an effort to solve the problems of the related art as described above. As a result, the present inventors confirmed that a peptide having both bone-forming capacity and binding capacity to apatite mineral can be present in a stable state when binding to a surface of apatite mineral, can promote transition, proliferation, and differentiation of cells associated with regeneration and eventually maximize bone tissue regeneration capacity, and exhibit high therapeutic effects in bone tissue regeneration, and then completed the present invention.

SUMMARY OF THE INVENTION

An object of the present invention is to provide a peptide having bone tissue regeneration capacity and binding to apatite, the peptide being stably immobilized to a surface of apatite mineral and retaining peptide activity.

Another object of the present invention is to provide a bone graft material and a biomaterial for bone regeneration, in which the peptide is immobilized to a surface of the apatite.

In order to achieve the foregoing objects, the present invention provides a peptide having bone tissue regeneration capacity and binding to apatite, in which a peptide having bone regeneration capacity and a peptide having apatite-binding capacity are linked to each other.

The present invention also provides a bone graft material and a biomaterial for bone regeneration, in which the peptide is immobilized to a surface of apatite.

DETAILED DESCRIPTION OF THE PREFERRED EMBODIMENTS

Figure 1:
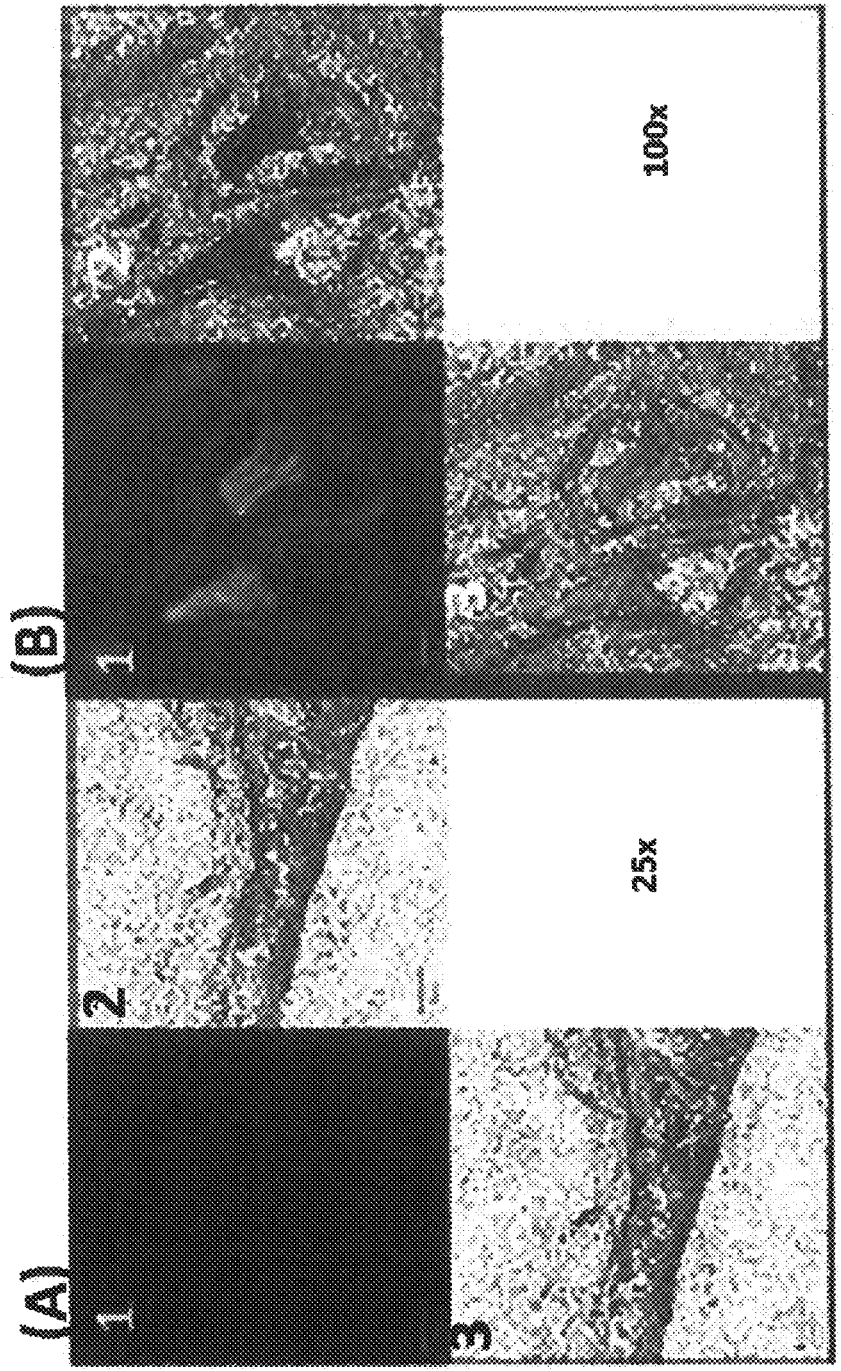
FIG. 1 shows images obtained when a tissue taken 4 weeks after grafting FITC-labeled bone mineral into the rabbit calvarial defect was observed by a confocal microscope (FIG. 1A for bone mineral without a binding peptide, and FIG. 1B for bone mineral with a binding peptide of SEQ ID NO: 40, labeled with FITC); "1" of both A and B represents confocal microscope image, "2" of both A and B represents DIC (differential interference contrast), and "3" of both A and B is a merge of each 1 and 2, respectively).

Unless defined otherwise, all the technical and scientific terms used herein have the same meanings as those generally understood by persons skilled in the art to which the present invention pertains. Generally, the nomenclature used herein are well known and commonly employed in the art.

In order to develop the peptide according to the present invention, amino acid sequences are extracted from active sites of the bone morphogenetic protein and extracellular matrix protein, and then subjected to chemical modification, to thereby retain an active structure.

An aspect of the present invention is directed to a peptide having bone tissue regeneration capacity and binding to apatite, in which at least one peptide selected from the group consisting of amino acid sequences of SEQ ID NO: 1 to SEQ ID NO: 35 and at least one peptide selected from the group consisting of amino acid sequences of SEQ ID NO: 36 to SEQ ID NO: 39 are lined to each other.

In the present invention, the peptide binding to apatite mineral may be selected from the group consisting of amino acid sequences of SEQ ID NO: 36 (STLPIPHEFSRE), SEQ ID NO: 37 (VTKHLNQISQSY), SEQ ID NO: 38 (SVSVGMKPSPRP), and SEQ ID NO: (NRVFEVLRCVFD). The peptide is chemically added to the N-terminus of the peptide having bone tissue generation capacity, to increase the binding capacity to apatite, which is a constituent of the bone, and thereby stably bind to a bone graft material or an implant coated with apatite.

In the present invention, the peptide having bone tissue regeneration capacity may be selected from the group consisting of amino acid sequences of SEQ ID NO: 1 to SEQ ID NO: 35.

Specifically, the peptide having bone tissue regeneration capacity may be at least one peptide selected from the group consisting of: a) amino acid sequence at positions 2-18 of each of the bone morphogenetic proteins (BMP)-2, 4 and 6 [SEQ ID NO: 1 for BMP-2, SEQ ID NO: 2 for BMP-4, and SEQ ID NO: 3 for BMP-6]; amino acid sequence at positions 16-34 (SEQ ID NO: 4), amino acid sequence at positions 47-71 (SEQ ID NO: 5), amino acid sequence at positions 73-92 (SEQ ID NO: 6), amino acid sequence at positions 88-105 (SEQ ID NO: 7), amino acid sequence at positions 83-302 (SEQ ID NO: 8), amino acid sequence at positions 335-353 (SEQ ID NO: 9) and amino acid sequence at positions 370-396 (SEQ ID NO: 10), of BMP-2; amino acid sequence at positions 74-93 (SEQ ID NO: 11), amino acid sequence at positions 293-313 (SEQ ID NO: 12), amino acid sequence at positions 360-379 (SEQ ID NO: 13) and amino acid sequence at positions 382-402 (SEQ ID NO: 14), of BMP-4; amino acid sequence at positions 91-110 (SEQ ID NO: 15), amino acid sequence at positions 407-418 (SEQ ID NO: 16), amino acid sequence at positions 472-490 (SEQ ID NO: 17) and amino acid sequence at positions 487-510 (SEQ ID NO: 18), of BMP-6; and amino acid sequence at positions 98-117 (SEQ ID NO: 19), amino acid sequence at positions 320-340 (SEQ ID NO: 20), amino acid sequence at positions 400-409 (SEQ ID NO: 21) and amino acid sequence at positions 405-423 (SEQ ID NO: 22), of BMP-7;

(b) amino acid sequence at positions 62-69 (SEQ ID NO: 23), amino acid sequence at positions 140-148 (SEQ ID NO: 24), amino acid sequence at positions 259-277 (SEQ ID NO: 25), amino acid sequence at positions 199-204 (SEQ ID NO: 26), amino acid sequence at positions 151-158 (SEQ ID NO: 27), amino acid sequence at positions 275-291 (SEQ ID NO: 28), amino acid sequence at positions 20-28 (SEQ ID NO: 29), amino acid sequence at positions 65-90 (SEQ ID NO: 30), amino acid sequence at positions 150-170 (SEQ ID NO: 31) and amino acid sequence at positions 280-290 (SEQ ID NO: 32), of bone sialoprotein II (BSP II); and (c) amino acid sequence at positions 149-169, YGLRSKS (SEQ ID NO: 33), KKFRRPDIQYPDAT (SEQ ID NO: 34), and YGLRSKSKKFRRPDIQYPDAT (SEQ ID NO: 35), of bone sialoprotein I (BSP I, osteopontin).

Another aspect of the present invention is directed to a bone graft material and a biomaterial for bone regeneration, in which a peptide having bone tissue regeneration capacity is immobilized on a surface of apatite.

In the present invention, the biomaterial for bone regeneration may be characterized by being selected from the group consisting of metals, natural polymers, and synthetic polymers.

In the present invention, in order to allow the peptide having bone tissue regeneration capacity and binding to apatite to bind to a surface of apatite of a bone graft material or a biomaterial for bone regeneration, a bone graft material composed of apatite or a biomaterial such as a metal, a natural polymer, or a synthetic polymer, having a surface coated with apatite, may be dipped in the peptide solution, and here, a chemical cross-linking agent for the binding is not needed.

The peptide having bone tissue regeneration capacity and binding to apatite according to the present invention is stably immobilized to the surface of apatite to thereby improve stability thereof and maintain activity thereof for a long time. Therefore, when the peptide is grafted into the body, the peptide is stably maintained at a local graft site to thereby retain the bone regeneration effect thereof, which is appropriate in the treatments for regenerating the bone tissue and periodontal tissue.

The peptide having bone tissue regeneration capacity and binding to apatite according to the present invention may bind to apatite selected from the group consisting of organism-derived hydroxylapatite bone minerals, synthetic hydroxyapatite, carbonated apatite, tricalcium phosphate, and monocalcium phosphate.

In the present invention, the peptide having bone tissue regeneration capacity and binding to apatite is preferably contained in a content of 1~100 mg per unit weight (1 g) of the bone graft material, and more preferably contained in a content of 20~80 mg per unit weight of the bone graft material.

In an embodiment of the present invention, a peptide of SEQ ID NO: 36 having apatite-binding capacity and a peptide of SEQ ID NO: 35 having bone tissue regeneration capacity were linked to each other, to manufacture a peptide of SEQ ID NO: 40 that has bone tissue regeneration capacity and binds to apatite. Then, it was checked whether or not the manufactured peptide stably bound to a bone graft material. In addition, the bone regeneration capacity was checked by grafting a bone graft material in which the peptide was stably immobilized on a surface of apatite into the calvarial defect.

EXAMPLES

Hereinafter, the present invention will be described in detail with reference to examples. These examples are only for exemplifying the present invention, and it will be obvious to those skilled in the art that the scope of the present invention is not construed to be limited to these examples.

Example 1

Preparation of Smart Peptide having Bone Tissue Regeneration Capacity and Specifically Binding to Surface of Apatite Mineral A peptide was synthesized by the F-moc solid phase chemical synthesis method using a peptide synthesizer, to contain YGLRSKSKKFRRPDIQYPDAT (SEQ ID NO: 35) as a sequence having bone regeneration capacity, derived from osteopontin, and STLPIPHEFSRE (SEQ ID NO: 36) as a peptide having apatite-binding capacity, sequentially from the N-terminus thereof. That is, the synthesis was conducted by using the Rink resin (0.075 mmol/g, 100~200 mesh, 1% DVB crosslinking) to which Fmoc-(9-Fluorenylmethoxycarbonyl) binds as a blocking group. 50 mg of the Rink resin was introduced into the synthesizer, and then subjected to swelling with DMF. After that, a 20% piperidine/DMF solution was used to remove the Fmoc-group. A 0.5M amino acid solution (solvent: DMF), a 1.0M DIPEA solution (solvent: DMF&NMP), and a 0.5M HBTU solution (solvent: DMF) were sequentially introduced in 5, 10, and 5 equivalents, respectively, from the C-terminus of the peptide, and then allowed to react for 1~2 hours under the nitrogen atmosphere. Whenever deprotection and coupling were ended, washing with DMF and NMP was carried out twice thereafter. Even after the final amino acid was coupled, deprotection was carried out to remove the Fmoc-group.

The ninhydrin test was used to confirm the synthesis. The resin tested and completely synthesized was dried over THF or DCM. Then, the TFA cleavage cocktail was input at a ratio of 20 ml per 1 g of resin, and then shaken for 3 hours, followed by filtering, to separate the resin and the cocktail with peptide dissolved therein. The solution filtered through the filter was removed by using a rotary evaporator and then cold ether was input thereto, or a large amount of cold ether was directly input to the TFA cocktail solution, to crystallize the peptide to a solid phase, which was then isolated by centrifugation. Here, the TFA cocktail was completely removed by washing several times with ether and centrifugation. The thus obtained peptide was dissolved in distilled water, and then freeze-dried.

```
(SEQ ID NO: 40)
NH2-STLPIPHEFSRE-YGLRSKSKKFRRPDIQYPDAT-COONH2.
```

After the synthesized peptide was cleaved from the resin and then washed and freeze-dried, it was isolated and purified by liquid chromatography. The purified peptide was subjected to MALDI analysis, to confirm the molecular weight thereof.

In order to test in vivo stability, 10 equivalents of fluorescein isothiocyanate (FITC) was allowed to bind to the N-terminus by using triethylamine (1 ml per 1 g of resin) at the time of preparing the peptide of SEQ ID NO: 40. The peptide synthesis was confirmed by measuring the molecular weight thereof through MALDI-TOF.

Example 2

Confirmation on In Vitro Stability of Smart Peptide Having Bone Tissue Regeneration Capacity and Specifically Binding to Surface of Apatite Mineral 1200 mg of the peptide prepared in Example 1 was dissolved in 1 mL of tertiary distilled water, and then 4 g of bovine bone mineral (OCS-B, NIBEC) was added thereto, followed by deposition for 24 hours and then freeze-drying.

4 g of a bone graft material with a binding peptide was input to 20 mL of PBS, and then the peptide release test was conducted at 37° C. After 7 days, 20 Ml of elution solvent that was initially introduced was completely removed, and then 20 Ml of new elution solvent was again added to proceed elution at 37° C. In the above manner, the peptide elution test was conducted for 14 days, 28 days, 56 days, 84 days, and 100 days. After completion of elution, the bone graft material was collected and the peptide content was measured.

Test Liquid Preparation Method 3 g of the bone graft material with a binding peptide was precisely weighed, and then made into powder. About 2 g of the powder corresponding to 160 mg of peptide was precisely weighed, which was then input to 40 mL of Solution A as mobile phase, followed by sonication for 1 hour. After that, extraction was conducted while stirring at 37±2° C. for 24 hours, and then the upper layer of the extracted solvent was separated by centrifuging at 3000 rpm for 10 minutes and then filtration with a 0.22 μm millipore filter. 1 mL thereof was taken therefrom, and mixed with 3 mL of Solution A, which was then filtered through a 0.22 μm millipore filter, then the filtrate was used as the test liquid.

Standard Liquid Preparation Method

The peptide standard product was dried in the desiccator (silica gel) for 5 hours, and then 10 mg thereof was precisely weighed, which was then dissolved by the addition of Solution A as a mobile phase, and then exactly 10 mL thereof was used as a standard liquid.

Test Method

The test liquid and the standard liquid each 10 μl were tested under the following operating conditions for liquid chromatography, to obtain test liquid and standard liquid peak areas, AT and AS.

Amount of peptide (mg)=amount of peptide standard product (mg)×

Operating Conditions

Meter: Analytical HPLC (Shimadzu, Japan)
Column: Filled with C18-bonded silica gel with 5 μm size (length: 250 nm, inner diameter: 4.6 mm)
Mobile phase: 0.1% trifluoroacetic acid/DDW (Solution A) 0.098% trifluoroacetic acid/acetonitrile (Solution B)
Detector: UV absorption spectrometer (measurement wavelength: 230 nm)
Flow rate: 1 ml/min
Column temperature: Constant at approximately 40° C.

TABLE 1

| Gradient Conditions: | |
|---|---|
| Time (min) | Composition of Solution B (%) |
| 1 | 5 |
| 35 | 100 |
| 45 | 100 |
| 50 | 5 |
| 60 | 5 |

The elution test was conducted for 100 days to measure the peak of the peptide in the elution liquid. As a result (FIG. 2), the peak of the peptide was not observed in Lot No. 1, 2, and 3 for the retention time of 14.196 min. After ending the elution, the amounts of peptide for Lot Nos. 1, 2, and 3 were measured at 9.2 mg, 9.18 mg, and 9.78 mg, respectively (FIG.

3). This proved that the peptide binding to the bone graft material was not released into the elution liquid, and thus the peptide was stably immobilized to the bone graft material.

TABLE 2

Result on Release of Peptide of SEQ ID NO: 40 from Bone Mineral

| Lot No. | day | Name | Ret. Time | Area | Height | mg |
|---|---|---|---|---|---|---|
| 1 | 7 | RT14.196 | 0.000 | 0 | 0 | 0 |
|  | 14 | RT14.196 | 0.000 | 0 | 0 | 0 |
|  | 28 | RT14.196 | 0.000 | 0 | 0 | 0 |
|  | 56 | RT14.196 | 0.000 | 0 | 0 | 0 |
|  | 84 | RT14.196 | 0.000 | 0 | 0 | 0 |
|  | 100 | RT14.196 | 0.000 | 0 | 0 | 0 |
| 2 | 7 | RT14.196 | 0.000 | 0 | 0 | 0 |
|  | 14 | RT14.196 | 0.000 | 0 | 0 | 0 |
|  | 28 | RT14.196 | 0.000 | 0 | 0 | 0 |
|  | 56 | RT14.196 | 0.000 | 0 | 0 | 0 |
|  | 84 | RT14.196 | 0.000 | 0 | 0 | 0 |
|  | 100 | RT14.196 | 0.000 | 0 | 0 | 0 |
| 3 | 7 | RT14.196 | 0.000 | 0 | 0 | 0 |
|  | 14 | RT14.196 | 0.000 | 0 | 0 | 0 |
|  | 28 | RT14.196 | 0.000 | 0 | 0 | 0 |
|  | 56 | RT14.196 | 0.000 | 0 | 0 | 0 |
|  | 84 | RT14.196 | 0.000 | 0 | 0 | 0 |
|  | 100 | RT14.196 | 0.000 | 0 | 0 | 0 |

TABLE 3

Content of Peptide of SEQ ID NO: 40 Remaining in Bone Mineral

| Lot No. | Name | Ret. Time | Area | Height | mg |
|---|---|---|---|---|---|
| 1 | RT14.196 | 14.244 | 1176751 | 51132 | 9.2 |
| 2 | RT14.196 | 14.235 | 1174499 | 51711 | 9.19 |
| 3 | RT14.196 | 14.229 | 124963 | 56018 | 9.78 |

Example 3

Confirmation on In Vivo Stability of Smart Peptide with Bone Tissue Regeneration Capacity and Specifically Binding to Surface of Apatite Mineral The peptide of SEQ ID NO: 40, labeled with FITC, was precipitated in the bovine bone mineral (OCS-B, NIBEC). The resultant bone mineral was grafted into the rabbit calvarial defect, and then scarified after 4 weeks. After that, the bone mineral grafted into the calvarial defect was observed by using a confocal microscope (Olympus, Japan). The bone mineral with a binding peptide of SEQ ID NO: 40, labeled with FITC, in 10 mg and 20 mg was grafted into the rabbit calvarial defect. The blood was taken before the graft and 1 day, 3 days, 7 days, 14 days, 21 days, and 28 days after the graft, and then it was determined by using the Fluorometer whether or not the peptide was freed into the systemic blood.

Figure 2:
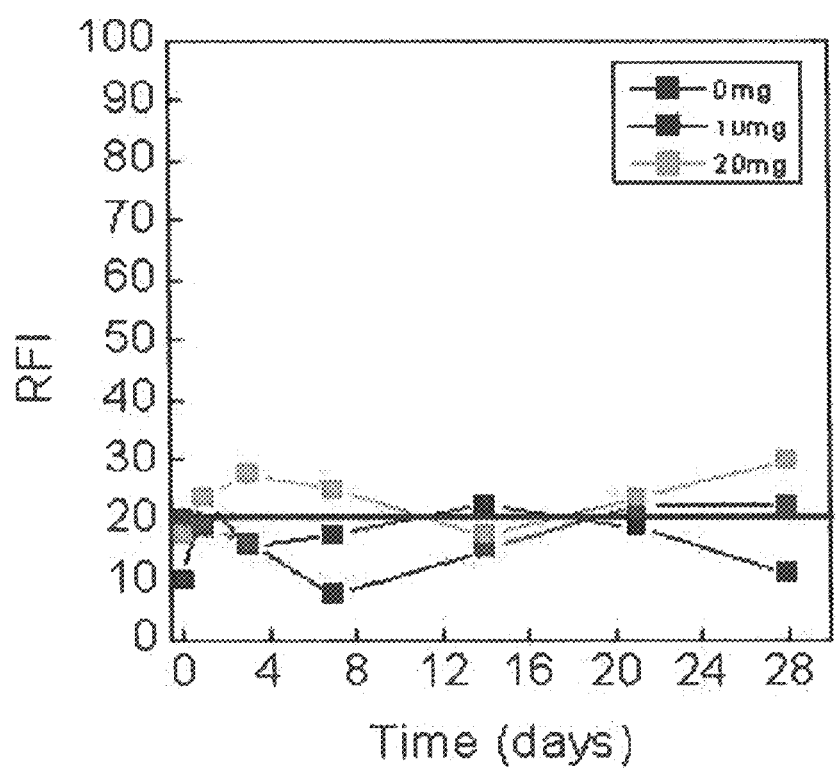
FIG. 2 shows results obtained when the blood is taken before and 1 day, 3 days, 7 days, 14 days, 21 days, and 28 days after grafting FITC-labeled bone mineral into the rabbit calvarial defect and then the peptides freed into the blood were measured by using a fluorometer (RFI: relative fluorescence index, straight line: plasma negative control, which shows measurement values by using plasma without a fluorescent material).

As a result, it was confirmed that the peptide was well immobilized on the surface of the bone graft material grafted into the calvarial defect and did not spread to the surrounding tissue (FIG. 1B). The RFI values had no differences as compared with the values before the graft, which confirmed that the peptide contained in the bone mineral was not freed in the blood, and this fact proved that the peptide was well immobilized on the surface of the bone mineral (FIG. 2).

Example 4

Confirmation on In Vivo Bone Regeneration Capacity of Smart Peptide with Bone Tissue Regeneration Capacity and Specifically Binding to Surface of Apatite Mineral Each of the peptides of SEQ ID NO: 35, SEQ ID NO: 36, and SEQ ID NO: 40, prepared in Example 1, was allowed to bind to a bone graft material by the same method as Example 2, which was then grafted into the rabbit calvarial defect. The bone regeneration capacity thereof was confirmed. An 8 mm-diameter circular bone defect was formed in the calvarial region of the anesthetized rabbit (NewZealand white rabbit, specific name: cuniculus). The bone graft material and the peptide-containing bone graft material were grafted into the bone defect with 50 mg for each defect, and the periosteum and skin were doubly sutured. The animal was sacrificed 2 weeks after the graft, and the taken sample was fixed in the formaline solution. The tissue was subjected to embedding to prepare a 20 µm-thick specimen. The prepared specimen was stained with basic fuchsin and toluidine blue to produce a nondemineralized sample. The thus produced sample was observed by an optical microscope, and photographed.

Figure 3:
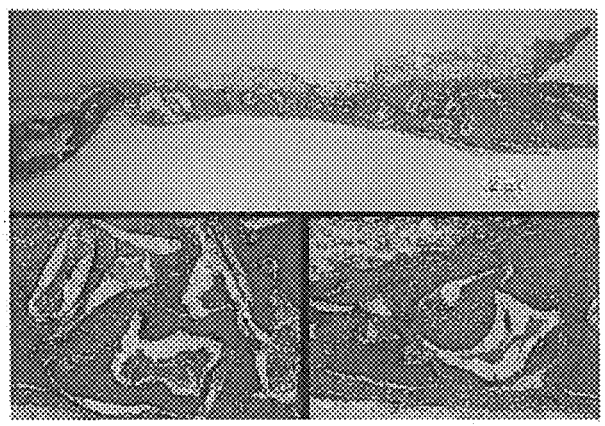
FIG. 3 shows images obtained by observing the degree of bone regeneration 2 weeks after grafting bone mineral with a binding peptide into the rabbit calvarial defect (FIG. 3A for a bone graft material with a binding peptide of SEQ ID NO: 36, FIG. 3B for a bone graft material with a binding peptide of SEQ ID NO: 35, and FIG. 3C for a bone graft material with a binding peptide of SEQ ID NO: 40 binds).
Figure 3:
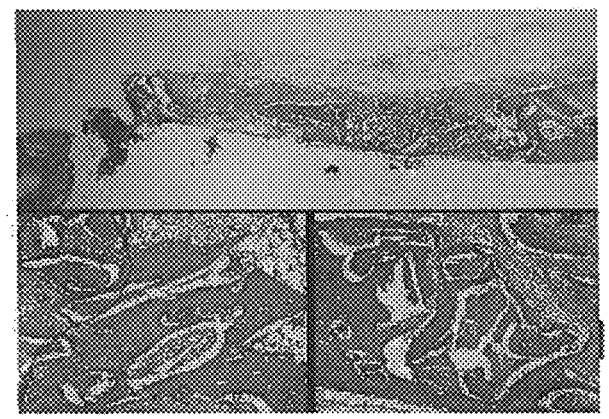
Figure 3:
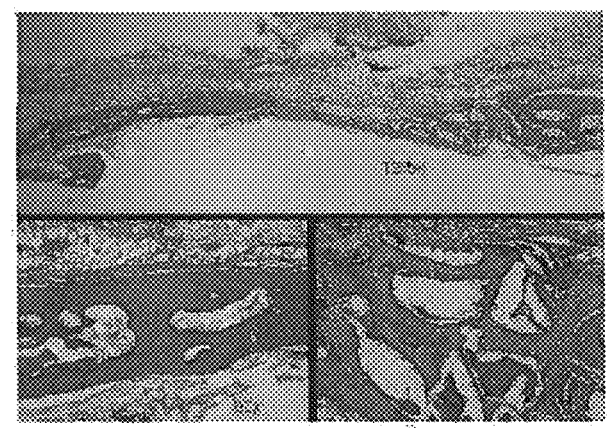

FIG. 3 shows the bone regeneration effect by the bone graft material containing a smart peptide that has bone tissue regeneration capacity and specifically binds to a surface of apatite mineral. The bone regeneration effect was smallest for the bone graft material with a binding peptide of SEQ ID NO: 36 (A, peptide binding to apatite). It was observed that the bone graft material with a binding peptide of SEQ ID NO: 35 (B, peptide having bone regeneration effect) had an increased bone regeneration effect as compared with A, and the bone graft material with a binding peptide of SEQ ID NO: 40 (C, smart peptide having bone rejuvenation capacity and specifically binding to the surface of apatite mineral) had a remarkably increased bone regeneration capacity as compared with A and B. It is proven therefrom that the peptide binding to apatite, itself, was not effective in the bone regeneration effect, and it is thought that the peptide having bone regeneration effect does not stably bind to the bone graft material and thus has a less bone regeneration effect as compared with the smart peptide having both capacities. Therefore, when the smart peptide having bone regeneration capacity and specifically binding to the surface of apatite mineral is used in the bone graft material made of apatite or the implant coated with apatite, the bone regeneration effect is anticipated to be great.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof. All modifications and variations of the present invention may be easily used by those skilled in the art, and these modifications or variations are construed to be included in the scope of the present invention.

The peptide having binding capacity to the apatite mineral and bone tissue regeneration capacity according to the present invention binds to the surface of apatite to thereby be present in a stable state, and thus can be used in a bone replacement material for dental or orthopedic application, and metal, natural polymers, or synthetic polymers, coated with apatite; promote transition, proliferation, and differentiation of cells associated with regeneration and eventually maximize bone tissue regeneration; and can be stably present while maintaining peptide activity when being grafted into the body and thus is useful in development of the bone tissue regeneration therapeutic technology using the peptide.

What is claimed is:

1. An isolated peptide having bone tissue regeneration capacity and binding to apatite, in which one peptide of amino acid sequence SEQ ID NO: 35 and one peptide of amino acid sequence SEQ ID NO: 36 are linked to each other.

2. A bone graft material in which the peptide of claim 1 is immobilized on a surface of apatite.

3. The bone graft material of claim 2, wherein the apatite is selected from the group consisting of organism-derived hydroxyapatite bone minerals, synthetic hydroxyapatite, carbonated apatite, tricalcium phosphate, and monocalcium phosphate.

4. The bone graft material of claim 2, wherein the peptide is contained in a content of 1~100 mg per unit weight (1 g) of the bone graft material.

5. A biomaterial for bone regeneration, in which the peptide of claim 1 is immobilized on a surface of apatite.

6. The biomaterial for bone regeneration of claim 5, wherein the biomaterial is selected from the group consisting of metals, natural polymers, and synthetic polymers.

7. The biomaterial for bone regeneration of claim 5, wherein the apatite is selected from the group consisting of organism-derived hydroxyapatite bone minerals, synthetic hydroxyapatite, carbonated apatite, tricalcium phosphate, and monocalcium phosphate.

8. The biomaterial for bone regeneration of claim 5, wherein the peptide is contained in a content of 1~100 mg per unit weight (1 g) of the biomaterial for bone regeneration.

9. A method for bone tissue regeneration, the method comprising the step of grafting the peptide according to claim 1 into a recipient site.

10. A method for bone tissue regeneration, the method comprising the step of grafting a composition containing the peptide according to claim 1 into a recipient site.

11. The method for bone tissue regeneration of claim 10, wherein the composition is a bone graft material or a biomaterial for bone regeneration.

12. An isolated peptide having bone tissue regeneration capacity and binding to apatite, wherein the peptide is represented by the amino acid sequence of SEQ ID NO: 40.

13. A bone graft material in which the peptide of claim 12 is immobilized on a surface of apatite.

14. The bone graft material of claim 13, wherein the apatite is selected from the group consisting of organism-derived hydroxyapatite bone minerals, synthetic hydroxyapatite, carbonated apatite, tricalcium phosphate, and monocalcium phosphate.

15. The bone graft material of claim 13, wherein the peptide is contained in a content of 1~100 mg per unit weight (1 g) of the bone graft material.

16. A biomaterial for bone regeneration, in which the peptide of claim 12 is immobilized on a surface of apatite.

17. The biomaterial for bone regeneration of claim 16, wherein the biomaterial is selected from the group consisting of metals, natural polymers, and synthetic polymers.

18. The biomaterial for bone regeneration of claim 16, wherein the apatite is selected from the group consisting of organism-derived hydroxyapatite bone minerals, synthetic hydroxyapatite, carbonated apatite, tricalcium phosphate, and monocalcium phosphate.

19. The biomaterial for bone regeneration of claim 16, wherein the peptide is contained in a content of 1~100 mg per unit weight (1 g) of the biomaterial for bone regeneration.

20. A method for bone tissue regeneration, the method comprising the step of grafting the peptide according to claim 15 into a recipient site.

21. A method for bone tissue regeneration, the method comprising the step of grafting a composition containing the peptide according to claim 12 into a recipient site.

22. The method for bone tissue regeneration of claim 21, wherein the composition is a bone graft material or a biomaterial for bone regeneration.

* * * * *

UNITED STATES PATENT AND TRADEMARK OFFICE
CERTIFICATE OF CORRECTION

| | |
|---|---|
| PATENT NO. | : 8,853,165 B2 |
| APPLICATION NO. | : 13/821811 |
| DATED | : October 7, 2014 |
| INVENTOR(S) | : Chung et al. |

Page 1 of 1

It is certified that error appears in the above-identified patent and that said Letters Patent is hereby corrected as shown below:

In the Claims,

Column 26, lines 28-29: "claim 15" should be -- claim 12 --.

Signed and Sealed this
Twenty-third Day of December, 2014

Michelle K. Lee
*Deputy Director of the United States Patent and Trademark Office*

SEQUENCE LISTING

<160> NUMBER OF SEQ ID NOS: 40

<210> SEQ ID NO 1
<211> LENGTH: 16
<212> TYPE: PRT
<213> ORGANISM: Artificial
<220> FEATURE:
<223> OTHER INFORMATION: partial peptide of BMP-2

<400> SEQUENCE: 1

Ala Lys His Lys Gln Arg Lys Arg Leu Lys Ser Ser Cys Lys Arg His
1               5                   10                  15

<210> SEQ ID NO 2
<211> LENGTH: 14
<212> TYPE: PRT
<213> ORGANISM: Artificial
<220> FEATURE:
<223> OTHER INFORMATION: partial peptide of BMP-4

<400> SEQUENCE: 2

Cys Ser Pro Lys His His Pro Gln Arg Ser Arg Lys Lys Asn
1               5                   10

<210> SEQ ID NO 3
<211> LENGTH: 13
<212> TYPE: PRT
<213> ORGANISM: Artificial
<220> FEATURE:
<223> OTHER INFORMATION: partial peptide of BMP-6

<400> SEQUENCE: 3

Cys Ser Ser Arg Lys Lys Asn Lys Asn Cys Arg Arg His
1               5                   10

<210> SEQ ID NO 4
<211> LENGTH: 17
<212> TYPE: PRT
<213> ORGANISM: Artificial
<220> FEATURE:
<223> OTHER INFORMATION: partial peptide of BMP-2

<400> SEQUENCE: 4

Ser Asp Val Gly Trp Asn Asp Trp Ile Val Ala Pro Pro Gly Tyr His
1               5                   10                  15

Ala

<210> SEQ ID NO 5
<211> LENGTH: 25
<212> TYPE: PRT
<213> ORGANISM: Artificial
<220> FEATURE:
<223> OTHER INFORMATION: partial peptide of BMP-2

<400> SEQUENCE: 5

Cys Pro Phe Pro Leu Ala Asp His Leu Asn Ser Thr Asn His Ala Ile
1               5                   10                  15

Val Gln Thr Leu Val Asn Ser Val Asn
            20                  25

<210> SEQ ID NO 6
<211> LENGTH: 20
<212> TYPE: PRT
<213> ORGANISM: Artificial
<220> FEATURE:
<223> OTHER INFORMATION: partial peptide of BMP-2

```
<400> SEQUENCE: 6

Lys Ile Pro Lys Ala Cys Cys Val Pro Thr Glu Leu Ser Ala Ile Ser
1               5                   10                  15

Met Leu Tyr Leu
            20

<210> SEQ ID NO 7
<211> LENGTH: 18
<212> TYPE: PRT
<213> ORGANISM: Artificial
<220> FEATURE:
<223> OTHER INFORMATION: partial peptide of BMP-2

<400> SEQUENCE: 7

Ser Met Leu Tyr Leu Asp Glu Asn Glu Lys Val Val Leu Lys Asn Tyr
1               5                   10                  15

Gln Asp

<210> SEQ ID NO 8
<211> LENGTH: 220
<212> TYPE: PRT
<213> ORGANISM: Artificial
<220> FEATURE:
<223> OTHER INFORMATION: partial peptide of BMP-2

<400> SEQUENCE: 8

Tyr Arg Arg His Ser Gly Gln Pro Gly Ser Pro Ala Pro Asp His Arg
1               5                   10                  15

Leu Glu Arg Ala Ala Ser Arg Ala Asn Thr Val Arg Ser Phe His His
                20                  25                  30

Glu Glu Ser Leu Glu Glu Leu Pro Glu Thr Ser Gly Lys Thr Thr Arg
            35                  40                  45

Arg Phe Phe Phe Asn Leu Ser Ser Ile Pro Thr Glu Glu Phe Ile Thr
        50                  55                  60

Ser Ala Glu Leu Gln Val Phe Arg Glu Gln Met Gln Asp Ala Leu Gly
65                  70                  75                  80

Asn Asn Ser Ser Phe His His Arg Ile Asn Ile Tyr Glu Ile Ile Lys
                85                  90                  95

Pro Ala Thr Ala Asn Ser Lys Phe Pro Val Thr Arg Leu Leu Asp Thr
            100                 105                 110

Arg Leu Val Asn Gln Asn Ala Ser Arg Trp Glu Ser Phe Asp Val Thr
        115                 120                 125

Pro Ala Val Met Arg Trp Thr Ala Gln Gly His Ala Asn His Gly Phe
    130                 135                 140

Val Val Glu Val Ala His Leu Glu Glu Lys Gln Gly Val Ser Lys Arg
145                 150                 155                 160

His Val Arg Ile Ser Arg Ser Leu His Gln Asp Glu His Ser Trp Ser
                165                 170                 175

Gln Ile Arg Pro Leu Leu Val Thr Phe Gly His Asp Gly Lys Gly His
            180                 185                 190

Pro Leu His Lys Arg Glu Lys Arg Gln Ala Lys His Lys Gln Arg Lys
        195                 200                 205

Arg Leu Lys Ser Ser Cys Lys Arg His Pro Leu Tyr
    210                 215                 220

<210> SEQ ID NO 9
<211> LENGTH: 20
```

-continued

```
<212> TYPE: PRT
<213> ORGANISM: Artificial
<220> FEATURE:
<223> OTHER INFORMATION: partial peptide of BMP-2

<400> SEQUENCE: 9

Lys Ile Pro Lys Ala Cys Cys Val Pro Thr Glu Leu Ser Ala Ile Ser
1               5                   10                  15

Met Leu Tyr Leu
            20

<210> SEQ ID NO 10
<211> LENGTH: 27
<212> TYPE: PRT
<213> ORGANISM: Artificial
<220> FEATURE:
<223> OTHER INFORMATION: partial peptide of BMP-2

<400> SEQUENCE: 10

Ser Met Leu Tyr Leu Asp Glu Asn Glu Lys Val Val Leu Lys Asn Tyr
1               5                   10                  15

Gln Asp Met Val Val Glu Gly Cys Gly Cys Arg
            20                  25

<210> SEQ ID NO 11
<211> LENGTH: 21
<212> TYPE: PRT
<213> ORGANISM: Artificial
<220> FEATURE:
<223> OTHER INFORMATION: partial peptide of BMP-4

<400> SEQUENCE: 11

Ser Ser Ile Pro Lys Ala Cys Cys Val Pro Thr Glu Leu Ser Ala Ile
1               5                   10                  15

Ser Met Leu Tyr Leu
            20

<210> SEQ ID NO 12
<211> LENGTH: 21
<212> TYPE: PRT
<213> ORGANISM: Artificial
<220> FEATURE:
<223> OTHER INFORMATION: partial peptide of BMP-4

<400> SEQUENCE: 12

Pro Lys His His Ser Gln Arg Ala Arg Lys Lys Asn Lys Asn Cys Arg
1               5                   10                  15

Arg His Ser Leu Tyr
            20

<210> SEQ ID NO 13
<211> LENGTH: 21
<212> TYPE: PRT
<213> ORGANISM: Artificial
<220> FEATURE:
<223> OTHER INFORMATION: partial peptide of BMP-4

<400> SEQUENCE: 13

Ser Ser Ile Pro Lys Ala Cys Cys Val Pro Thr Glu Leu Ser Ala Ile
1               5                   10                  15

Ser Met Leu Tyr Leu
            20

<210> SEQ ID NO 14
```

```
<211> LENGTH: 21
<212> TYPE: PRT
<213> ORGANISM: Artificial
<220> FEATURE:
<223> OTHER INFORMATION: partial peptide of BMP-4

<400> SEQUENCE: 14

Ser Met Leu Tyr Leu Asp Glu Tyr Asp Lys Val Val Leu Lys Asn Tyr
1               5                   10                  15

Gln Glu Met Val Val
            20

<210> SEQ ID NO 15
<211> LENGTH: 20
<212> TYPE: PRT
<213> ORGANISM: Artificial
<220> FEATURE:
<223> OTHER INFORMATION: partial peptide of BMP-6

<400> SEQUENCE: 15

Tyr Val Pro Lys Pro Cys Cys Ala Pro Thr Lys Leu Asn Ala Ile Ser
1               5                   10                  15

Val Leu Tyr Phe
            20

<210> SEQ ID NO 16
<211> LENGTH: 12
<212> TYPE: PRT
<213> ORGANISM: Artificial
<220> FEATURE:
<223> OTHER INFORMATION: partial peptide of BMP-6

<400> SEQUENCE: 16

Glu Leu Lys Thr Ala Cys Arg Lys His Glu Leu Tyr
1               5                   10

<210> SEQ ID NO 17
<211> LENGTH: 20
<212> TYPE: PRT
<213> ORGANISM: Artificial
<220> FEATURE:
<223> OTHER INFORMATION: partial peptide of BMP-6

<400> SEQUENCE: 17

Tyr Val Pro Lys Pro Cys Cys Ala Pro Thr Lys Leu Asn Ala Ile Ser
1               5                   10                  15

Val Leu Tyr Phe
            20

<210> SEQ ID NO 18
<211> LENGTH: 24
<212> TYPE: PRT
<213> ORGANISM: Artificial
<220> FEATURE:
<223> OTHER INFORMATION: partial peptide of BMP-6

<400> SEQUENCE: 18

Ser Val Leu Tyr Phe Asp Asp Asn Ser Asn Val Ile Leu Lys Lys Tyr
1               5                   10                  15

Arg Asn Met Val Val Arg Ala Cys
            20

<210> SEQ ID NO 19
<211> LENGTH: 20
<212> TYPE: PRT
```

```
<213> ORGANISM: Artificial
<220> FEATURE:
<223> OTHER INFORMATION: Partial sequence of BMP-7

<400> SEQUENCE: 19

Thr Val Pro Lys Pro Cys Cys Ala Pro Thr Gln Leu Asn Ala Ile Ser
1               5                   10                  15

Val Leu Tyr Phe
            20

<210> SEQ ID NO 20
<211> LENGTH: 21
<212> TYPE: PRT
<213> ORGANISM: Artificial
<220> FEATURE:
<223> OTHER INFORMATION: Partial peptide of BMP-7

<400> SEQUENCE: 20

Glu Asn Ser Ser Ser Asp Gln Arg Gln Ala Cys Lys Lys His Glu Leu
1               5                   10                  15

Tyr Val Ser Phe Arg
            20

<210> SEQ ID NO 21
<211> LENGTH: 10
<212> TYPE: PRT
<213> ORGANISM: Artificial
<220> FEATURE:
<223> OTHER INFORMATION: Partial peptide of BMP-7

<400> SEQUENCE: 21

Gln Leu Asn Ala Ile Ser Val Leu Tyr Phe
1               5                   10

<210> SEQ ID NO 22
<211> LENGTH: 19
<212> TYPE: PRT
<213> ORGANISM: Artificial
<220> FEATURE:
<223> OTHER INFORMATION: Partial peptide of BMP-7

<400> SEQUENCE: 22

Ser Val Leu Tyr Phe Asp Asp Ser Ser Asn Val Ile Leu Lys Lys Tyr
1               5                   10                  15

Arg Asn Met

<210> SEQ ID NO 23
<211> LENGTH: 8
<212> TYPE: PRT
<213> ORGANISM: Artificial
<220> FEATURE:
<223> OTHER INFORMATION: partial peptide of bone sialoprotein

<400> SEQUENCE: 23

Glu Glu Glu Gly Glu Glu Glu Glu
1               5

<210> SEQ ID NO 24
<211> LENGTH: 45
<212> TYPE: PRT
<213> ORGANISM: Artificial
<220> FEATURE:
<223> OTHER INFORMATION: partial peptide of bone sialoprotein

<400> SEQUENCE: 24
```

-continued

```
Asn Thr Thr Leu Ser Ala Thr Thr Leu Gly Tyr Gly Glu Asp Ala Thr
1               5                   10                  15
Pro Gly Thr Gly Tyr Thr Gly Leu Ala Ala Ile Gln Leu Pro Lys Lys
                20                  25                  30
Ala Gly Asp Ile Thr Asn Lys Ala Thr Lys Glu Lys Glu
            35                  40                  45

<210> SEQ ID NO 25
<211> LENGTH: 18
<212> TYPE: PRT
<213> ORGANISM: Artificial
<220> FEATURE:
<223> OTHER INFORMATION: partial peptide of bone sialoprotein

<400> SEQUENCE: 25

Tyr Glu Thr Tyr Asp Glu Asn Asn Gly Glu Pro Arg Gly Asp Thr Tyr
1               5                   10                  15
Arg Ile

<210> SEQ ID NO 26
<211> LENGTH: 6
<212> TYPE: PRT
<213> ORGANISM: Artificial
<220> FEATURE:
<223> OTHER INFORMATION: partial peptide of bone sialoprotein

<400> SEQUENCE: 26

Glu Glu Gly Glu Glu Glu
1               5

<210> SEQ ID NO 27
<211> LENGTH: 8
<212> TYPE: PRT
<213> ORGANISM: Artificial
<220> FEATURE:
<223> OTHER INFORMATION: partial peptide of bone sialoprotein

<400> SEQUENCE: 27

Glu Glu Glu Glu Glu Glu Glu Glu
1               5

<210> SEQ ID NO 28
<211> LENGTH: 17
<212> TYPE: PRT
<213> ORGANISM: Artificial
<220> FEATURE:
<223> OTHER INFORMATION: partial peptide of bone sialoprotein

<400> SEQUENCE: 28

Tyr Glu Ile Tyr Glu Ser Glu Asn Gly Glu Pro Arg Gly Asp Asn Tyr
1               5                   10                  15
Arg

<210> SEQ ID NO 29
<211> LENGTH: 9
<212> TYPE: PRT
<213> ORGANISM: Artificial
<220> FEATURE:
<223> OTHER INFORMATION: partial peptide of bone sialoprotein

<400> SEQUENCE: 29

Lys Asn Leu His Arg Arg Val Lys Ile
1               5
```

```
<210> SEQ ID NO 30
<211> LENGTH: 26
<212> TYPE: PRT
<213> ORGANISM: Artificial
<220> FEATURE:
<223> OTHER INFORMATION: partial peptide of bone sialoprotein

<400> SEQUENCE: 30

Asp Ser Ser Glu Glu Asn Gly Asp Asp Ser Ser Glu Glu Glu Glu Glu
1               5                   10                  15

Glu Glu Glu Thr Ser Asn Glu Gly Glu Asn
            20                  25

<210> SEQ ID NO 31
<211> LENGTH: 21
<212> TYPE: PRT
<213> ORGANISM: Artificial
<220> FEATURE:
<223> OTHER INFORMATION: partial peptide of bone sialoprotein

<400> SEQUENCE: 31

Asp Glu Glu Glu Glu Glu Glu Glu Gly Asn Glu Asn Glu Glu Ser
1               5                   10                  15

Glu Ala Glu Val Asp
            20

<210> SEQ ID NO 32
<211> LENGTH: 11
<212> TYPE: PRT
<213> ORGANISM: Artificial
<220> FEATURE:
<223> OTHER INFORMATION: partial peptide of bone sialoprotein

<400> SEQUENCE: 32

Ser Glu Asn Gly Glu Pro Arg Gly Asp Asn Tyr
1               5                   10

<210> SEQ ID NO 33
<211> LENGTH: 7
<212> TYPE: PRT
<213> ORGANISM: Artificial
<220> FEATURE:
<223> OTHER INFORMATION: partial peptide of bone sialoprotein

<400> SEQUENCE: 33

Tyr Gly Leu Arg Ser Lys Ser
1               5

<210> SEQ ID NO 34
<211> LENGTH: 14
<212> TYPE: PRT
<213> ORGANISM: Artificial
<220> FEATURE:
<223> OTHER INFORMATION: partial peptide of bone sialoprotein

<400> SEQUENCE: 34

Lys Lys Phe Arg Arg Pro Asp Ile Gln Tyr Pro Asp Ala Thr
1               5                   10

<210> SEQ ID NO 35
<211> LENGTH: 21
<212> TYPE: PRT
<213> ORGANISM: Artificial
<220> FEATURE:
<223> OTHER INFORMATION: partial peptide of bone sialoprotein

<400> SEQUENCE: 35
```

Tyr Gly Leu Arg Ser Lys Ser Lys Phe Arg Arg Pro Asp Ile Gln
1               5                   10                  15

Tyr Pro Asp Ala Thr
                20

<210> SEQ ID NO 36
<211> LENGTH: 12
<212> TYPE: PRT
<213> ORGANISM: Artificial
<220> FEATURE:
<223> OTHER INFORMATION: apatite binding peptide

<400> SEQUENCE: 36

Ser Thr Leu Pro Ile Pro His Glu Phe Ser Arg Glu
1               5                   10

<210> SEQ ID NO 37
<211> LENGTH: 12
<212> TYPE: PRT
<213> ORGANISM: Artificial
<220> FEATURE:
<223> OTHER INFORMATION: aptite binding peptide

<400> SEQUENCE: 37

Val Thr Lys His Leu Asn Gln Ile Ser Gln Ser Tyr
1               5                   10

<210> SEQ ID NO 38
<211> LENGTH: 12
<212> TYPE: PRT
<213> ORGANISM: Artificial
<220> FEATURE:
<223> OTHER INFORMATION: aptite binding peptide

<400> SEQUENCE: 38

Ser Val Ser Val Gly Met Lys Pro Ser Pro Arg Pro
1               5                   10

<210> SEQ ID NO 39
<211> LENGTH: 12
<212> TYPE: PRT
<213> ORGANISM: Artificial
<220> FEATURE:
<223> OTHER INFORMATION: apatite binding peptide

<400> SEQUENCE: 39

Asn Arg Val Phe Glu Val Leu Arg Cys Val Phe Asp
1               5                   10

<210> SEQ ID NO 40
<211> LENGTH: 33
<212> TYPE: PRT
<213> ORGANISM: Artificial
<220> FEATURE:
<223> OTHER INFORMATION: apatite binding smart peptide

<400> SEQUENCE: 40

Ser Thr Leu Pro Ile Pro His Glu Phe Ser Arg Glu Tyr Gly Leu Arg
1               5                   10                  15

Ser Lys Ser Lys Lys Phe Arg Arg Pro Asp Ile Gln Tyr Pro Asp Ala
            20                  25                  30

Thr